(12) United States Patent
Avaltroni

(10) Patent No.: US 6,221,030 B1
(45) Date of Patent: Apr. 24, 2001

(54) AUTOMATIC BIOPSY DEVICE

(75) Inventor: Paolo Avaltroni, Mantova (IT)

(73) Assignee: Gallini S.r.l., Modena (IT)

( * ) Notice: Subject to any disclaimer, the term of this patent is extended or adjusted under 35 U.S.C. 154(b) by 0 days.

(21) Appl. No.: 09/452,715

(22) Filed: Dec. 2, 1999

(30) Foreign Application Priority Data

Dec. 4, 1998 (IT) .............................................. B098A0688

(51) Int. Cl.[7] .................................................. A61B 10/00
(52) U.S. Cl. ............................................................ 600/567
(58) Field of Search ................................... 600/567, 568, 600/562

(56) References Cited

U.S. PATENT DOCUMENTS

| | | | |
|---|---|---|---|
| 5,752,923 | * | 5/1998 | Terwilliger ............................ 600/562 |
| 5,980,469 | * | 11/1999 | Burbank et al. ...................... 600/567 |
| 5,993,399 | * | 11/1999 | Pruitt et al. ........................... 600/567 |

\* cited by examiner

Primary Examiner—John P. Lacyk
Assistant Examiner—Brian Szmal
(74) Attorney, Agent, or Firm—William J. Sapone; Coleman Sudol Sapone, P.C.

(57) ABSTRACT

An automatic biopsy device includes a needle formed by a cannula and a stylet which is sliding axially inside the cannula and which is equipped with a cavity for receiving a sample of the organ to be examined. The device includes a first moving element and a second moving element mounted slidingly inside a box-like covering and aimed at being fastened respectively to a proximal end of the stylet and to a proximal end of the cannula of the needle. The first moving element and the second moving element are fastened by flexible means to a first cam and to a second cam, respectively. The cams rotate, independently one from the other, about a transversal axis of the covering. A first loading lever and a second loading lever, are pivoted to the covering and drive to rotate, the first cam and the second cam, respectively, against elastic means, so as to move to a loading position the first moving element and the second moving element. A first locking and second locking keep the first moving element and second moving element in a loading position and are released in sequence by button means, in order to control the ejection of the needle.

14 Claims, 6 Drawing Sheets

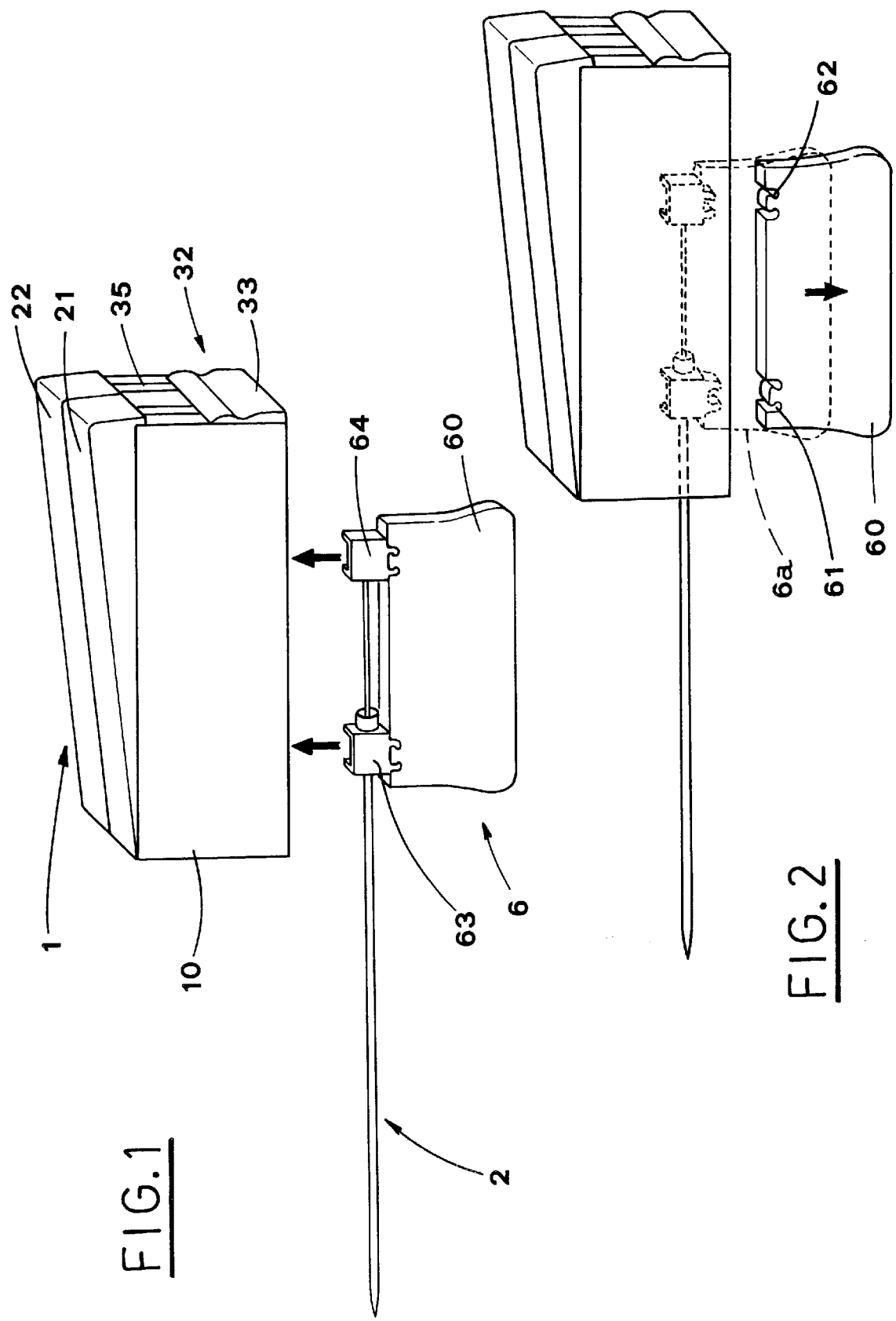

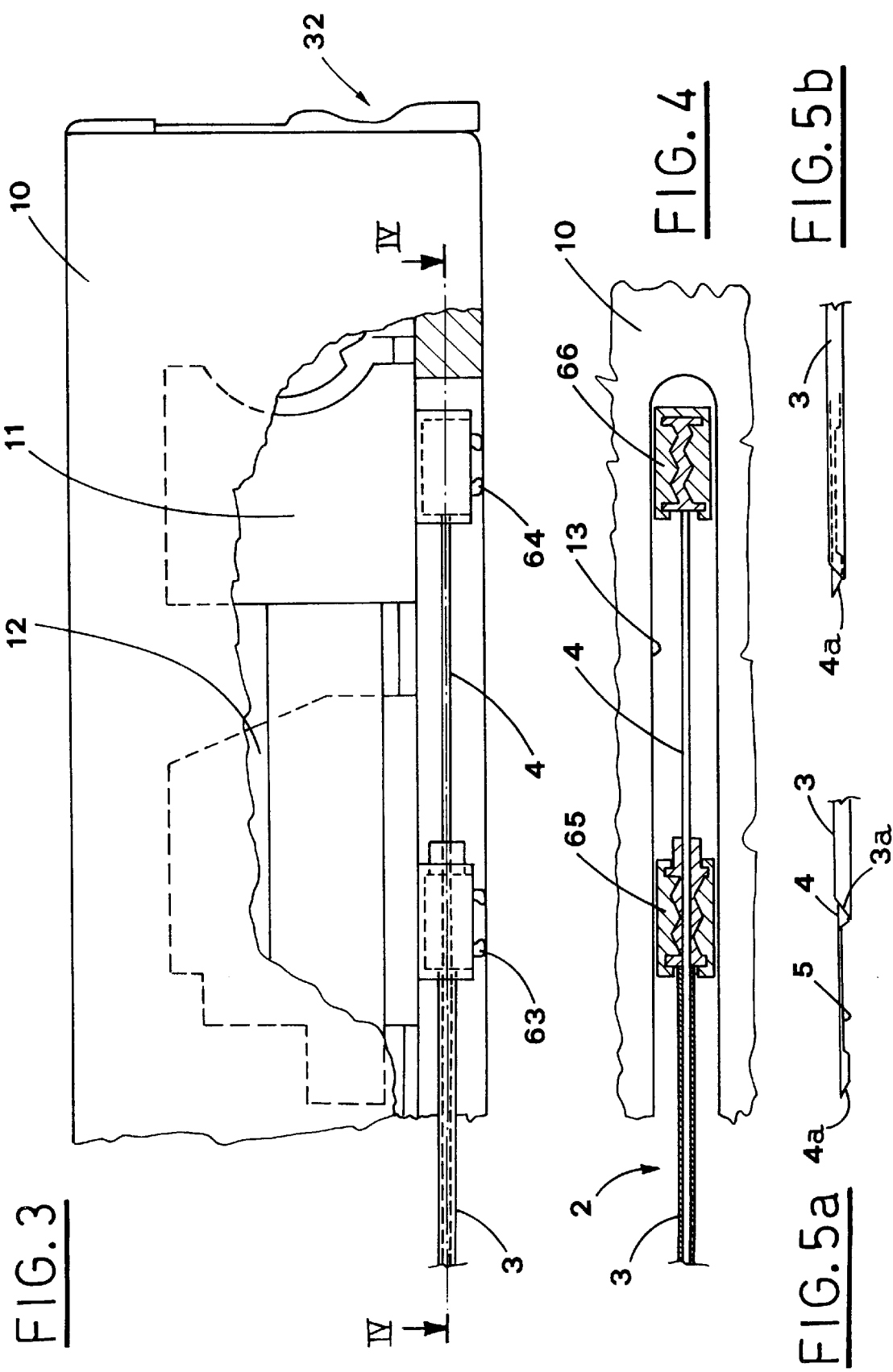

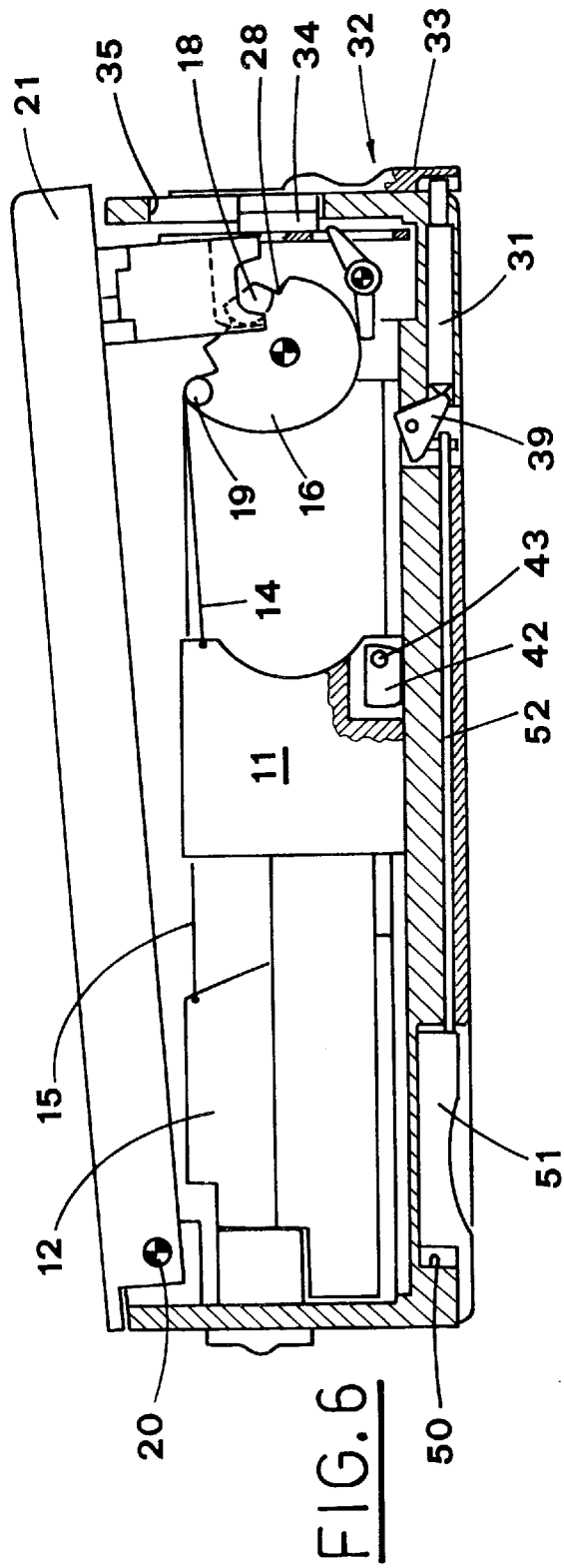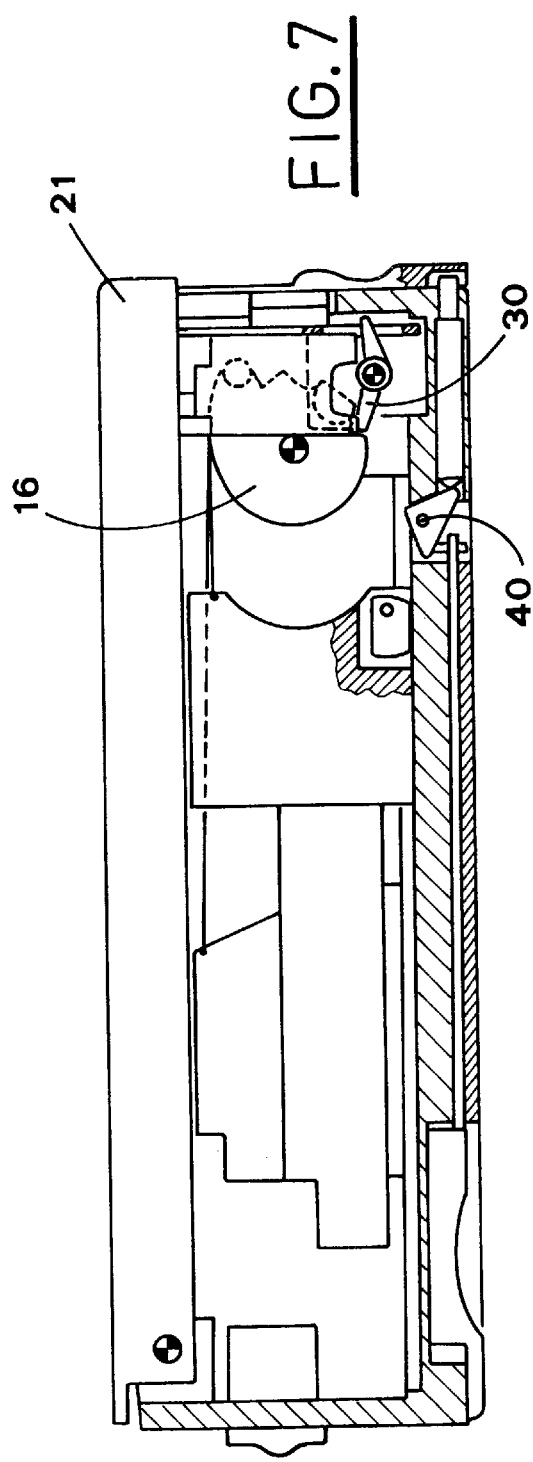

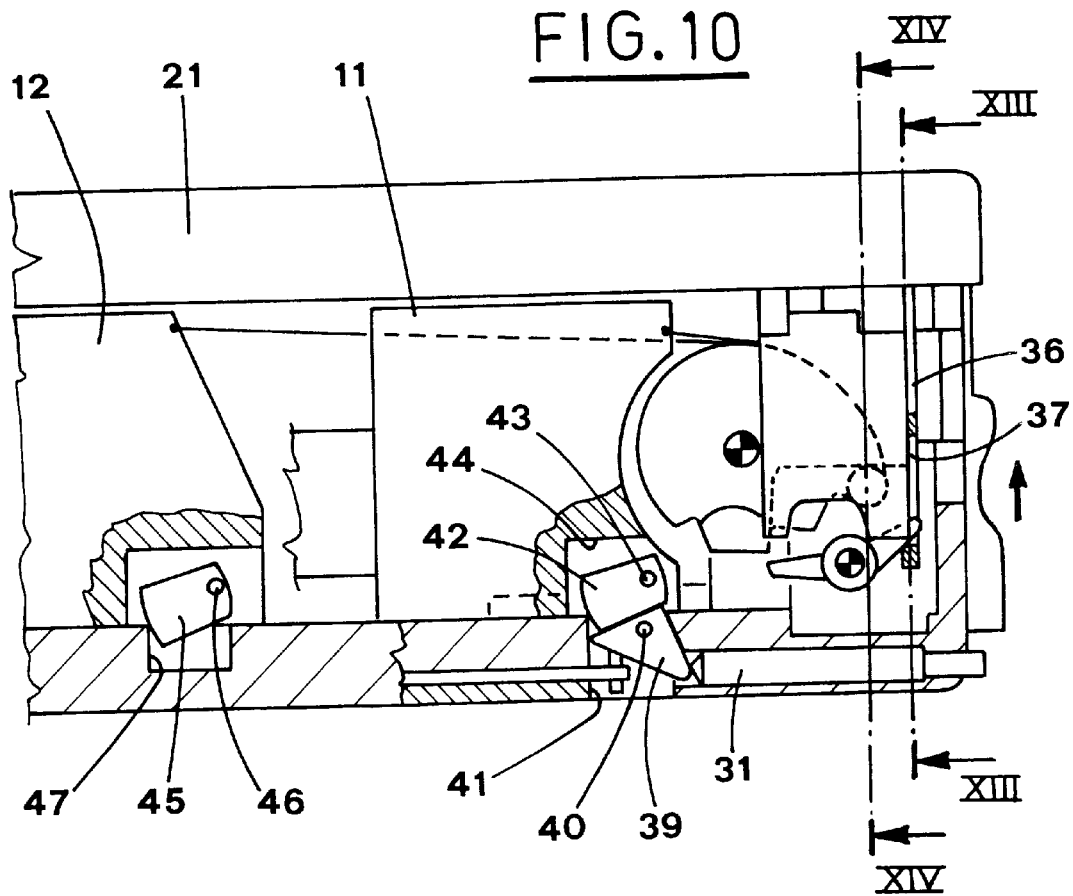
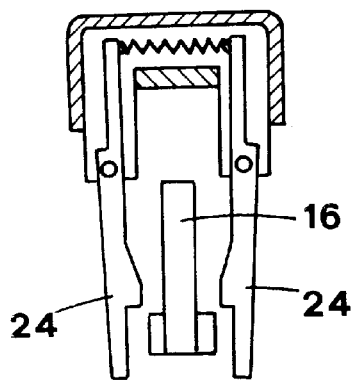
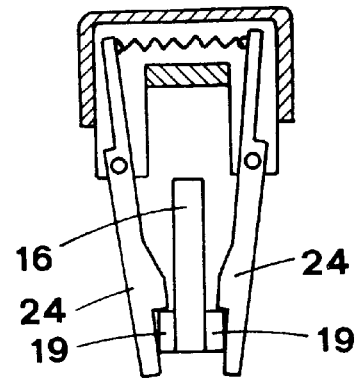
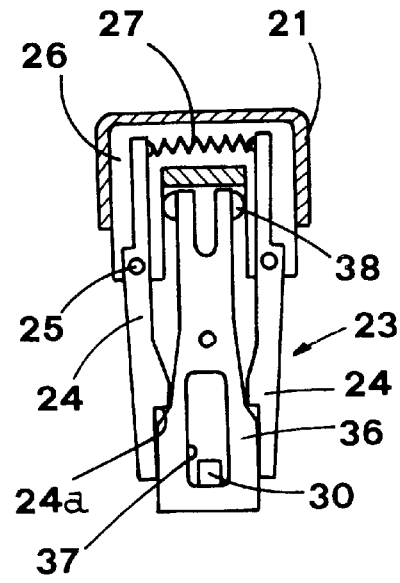

AUTOMATIC BIOPSY DEVICE

TECHNICAL FIELD

The present invention relates to the production of surgical instruments for transcutaneous biopsy. The biopsy are made by sampling the tissue of the organ to be examined.

In particular, the invention relates to a needle device for automatic sampling soft tissues.

BACKGROUND ART

Automatic devices for transcutaneous biopsy have heretofore been provided, which use suitable needles for sampling tissues.

In particular, the biopsy needles usually include a cannula that has a sharp edge at its distal end.

A rod or stylet with a suitably pointed distal end is slidably inserted into the cannula. The pointed end of the stylet goes out of the cannula when the first is wholly inserted in the latter.

At its pointed distal end, the stylet features also a longitudinal cavity for receiving a bioptic sample of tissue to be examined.

The needle is usually used during the patient's complete anesthesia and under control of radiographic and ultrasonographic monitoring and visualization means.

The needle is introduced through the skin until the pointed distal end, protruding from the cannula, partially penetrates the tissue to be analyzed.

Then, the stylet is moved quickly forward for a predetermined length, to introduce the above mentioned cavity into the tissue.

Afterwards, the outer cannula is moved quickly forward, so that the sharp edge thereof cuts the portion of tissue contained in the cavity of the stylet like a guillotine; the portion of the tissue thus obtained is closed and kept in the cavity of the stylet.

Then, the needle is withdrawn and the bioptic sample is removed.

Automatic biopsy devices currently used, have a moving element which slides within a box-like covering and supports the cannula and the stylet of the needle, which are subjected to elastic reaction, usually created by related springs.

The springs, previously loaded and operated by a suitable push button, allow the stylet and the cannula to move quickly forward in a proper order.

In practice, the above described devices can automatically carry out a first working step, in which the stylet moves forward and its distal end is uncovered by withdrawing a predetermined portion of the stylet from the cannula, and a second working step, in which the cannula cuts the portion of the tissue contained between the stylet cavity and the inner wall of the cannula, while the cannula slides on the stylet, until the cavity of the stylet is wholly unloaded.

In the step in which the device is loaded, the cavity of the stylet is inside the cannula. During the loading step, a safety catch is possibly automatically inserted to avoid incidental operation of the device, and then the springs are loaded to expel the needle later on.

During the needle ejection, after the safety catch has been removed and the needle has been introduced into the organ to be examined, the operation button is pressed, so as to move forward first the stylet and then the cannula, due to the unloading action of the springs on respective moving elements, as described above.

Reported disadvantages of above described devices derive from irksome and difficult loading of the springs. The springs are loaded by e.g. mutual rotation of two portions of the box-like covering, by means of a kinetic mechanism for loading the springs activated by a series of helical guides, or by axial sliding of a suitable cursor.

In any case, loading of the springs involves the operator's both hands and requires a considerable effort, due to the resistance of the springs, which must have considerable elastic force for the subsequent needle ejection step.

Moreover, the springs loading mechanisms are often complicated and their use is difficult, because the operator must take practice of all the necessary operations and needs a fairly good specific manual ability.

Another drawback of the known needle devices lies in the fact that also the introduction of the needle requires a quite big number of operations, because e.g. a lid of the box-like covering must be previously opened.

SUMMARY OF THE INVENTION

The object of the present invention is to propose an automatic needle device, which allows to perform a biopsy of soft tissues in best way, and by which in particular, the operator can load the mechanism, with one hand only.

Another object of the present invention is to propose a needle device for biopsy, which facilitates the introduction of the needle.

A further object of the present invention is to propose a needle device, which is simple to manufacture, and whose use is safe and precise.

The above mentioned objects are obtained, in accordance with the contents of claims, by means of an automatic biopsy device, including:

a needle formed by a cannula, having a cannula distal end with a cutting rim, and a cannula proximal end;

a stylet sliding axially inside said cannula and having a stylet distal end with a pointed portion, and a stylet proximal end, said pointed portion protruding from said cannula distal end of said cannula when the stylet is in an advanced position;

a cavity made in said stylet close to said stylet distal end and aimed at receiving a sample of an organ to be examined;

a box-like covering;

a first moving element mounted slidingly inside said box-like covering and aimed at being fastened to said stylet proximal end of said stylet of said needle;

a second moving element mounted slidingly inside said box-like covering beside said first moving element and aimed at being fastened to said cannula proximal end of said cannula of said needle;

a first cam and a second cam rotating, independently one from the other, about a transversal axis of said covering, and fastened by flexible means to said moving element and to said second moving element, respectively;

a first loading lever and a second loading lever arranged side by side and pivoted to said covering, said first loading lever and second loading lever being aimed at driving said first cam and said second cam respectively, into rotation against elastic means, so as to move said first moving element and said second moving element to a loading position;

first locking means and second locking means for keeping said first moving element and said second moving element, respectively, in said loading position;

button means for releasing said locking means in said loading position, to operate an ejection of the needle.

BRIEF DESCRIPTION OF THE DRAWINGS

The characteristics of the present invention are pointed out in the following detailed description taken in conjunction with the accompanying drawings, in which:

FIG. 1 is a perspective view of the proposed biopsy needle device, during the introduction of the needle;

FIG. 2 is a perspective view of the same biopsy needle device, while being used;

FIG. 3 shows the biopsy device in a lateral partially broken view, as to let see out the inner parts;

FIG. 4 is a corresponding plan view along the plane IV—IV of FIG. 3;

FIGS. 5a and 5b are partial views of the needle, respectively with the stylet expelled from the cannula and introduced therein;

FIG. 6 is a longitudinal section view of the device without the needle, in the rest position;

FIGS. 7, 8 and 9 are longitudinal section views of the device, in subsequent loading steps;

FIGS. 10, 11 and 12 are partial section enlarged views of the device, in subsequent steps of the needle operation;

FIG. 13 is a corresponding cross-section view taken along the plane XIII—XIII of FIG. 10;

FIGS. 14a and 14b are cross-section views, taken along the plane XIV—XIV of the FIG. 10, in different working positions.

DISCLOSURE OF THE INVENTION

Figure 8:
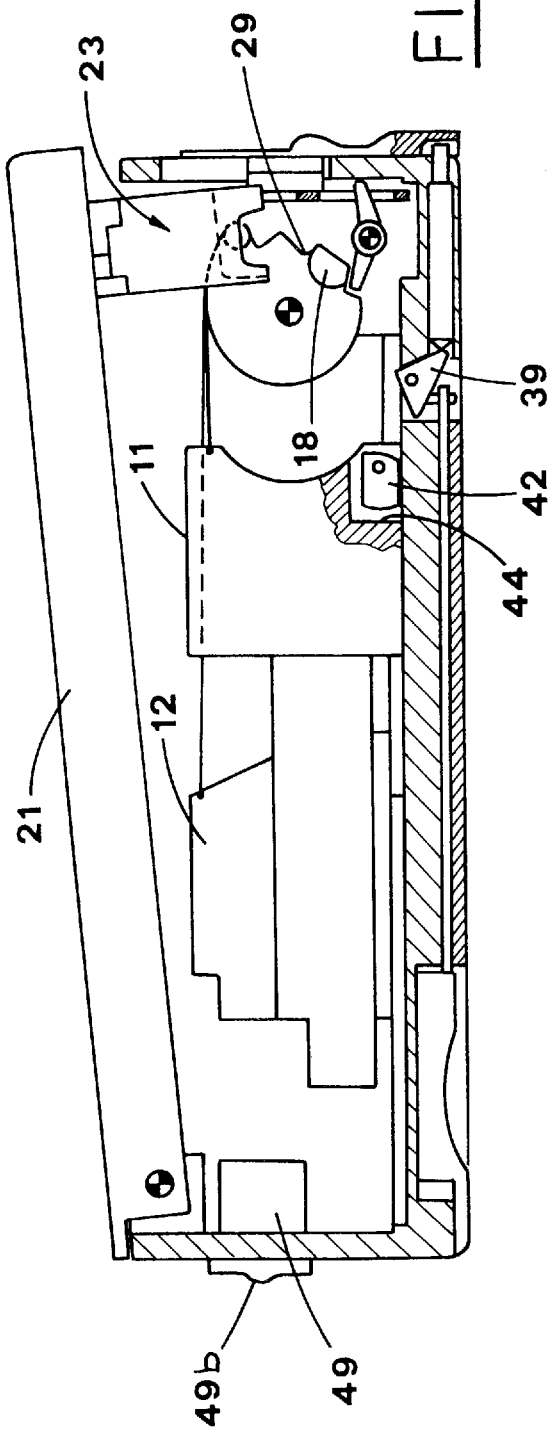

With reference to the above described figures, reference numeral 1 generally designates a biopsy device, specially for soft tissues biopsy, equipped with a needle 2.

The needle 2 includes a substantially cylindrical cannula 3 made of metallic material, whose distal end 3a features a cutting rim, which facilitates the penetration in the tissue (FIGS. 5a and 5b).

A cylindrical stylet 4 slides axially inside the cannula 3 and includes, at a distal end thereof, a pointed portion 4a, which protrudes from the corresponding distal end 3a of the cannula 3, when the stylet is in an advanced position.

The stylet 4 features a cavity 5, made in known way at its distal end for receiving a sample of the organ to be examined by the biopsy.

The device 1 includes a box-like covering 10, inside which two moving elements, a first moving element 11 and a second moving element 12, are mounted one beside the other and slide along suitable guides.

The moving elements 11, 12 are axially stressed by relative elastic means, which include a pair of extension springs, which are known and not shown for the sake of clarity.

The proximal end of the stylet 4 of the needle 2 is fastened to the first moving element 11, as will be better explained later, while the proximal end of the cannula 3 is fastened to the second moving element 12.

The needle is introduced in a longitudinal groove 13 made in the lower part of the box-like covering 10 (FIGS. 3 and 4).

The first moving element 11 is fastened to a first cam 16 by relative first flexible means 14, while the second moving element 12 is fastened to a second cam 17 by relative second flexible means 15.

The first and second flexible means 14, 15 are preferably strips made of steel.

The first cam 16 and the second cam 17 rotate, independently one from the other, about a transversal axis of the covering 10.

The cams 16, 17 are driven into rotation to shift the moving elements 11, 12 to a loading position, by a corresponding pair of loading levers 21, 22 arranged side by side along the upper part of the covering 10 and pivoted on the pin 20 of the same covering 10.

The levers 21, 22 are kept in a normally raised position by elastic means, not shown.

The first and second cams 16, 17 have respectively a first and a second pair of protrusions 18, 19 which are protruding from both sides of the cams 16, 17 and which are to be engaged by the relative gripping means 23 supported by the loading levers 21 and 22.

The gripping means 23 include pliers formed by a pair of oscillating prongs 24, which are pivoted to a connection pieces 26, by means of related pins 25. The connection pieces 26 are respectively joined to the levers 21 and 22 (FIG. 13).

The prongs 24 are maintained in a normally closed position by a return spring 27 (FIG. 14b).

The inner side of the prongs 24 form respective shoulders 24a, which engage with the protrusions 18, 19 of the cams 16, 17.

The cams 16 and 17 form also recesses 28, 29, adjacent to the above mentioned protrusions 18, 19. The recesses 28, 29 engage with a rocker arm 30, which rotates about a transversal axis of the covering 10.

The needle device is operated by a push button 31, mounted slidingly in a proper seat made in the lower part of the covering 10.

The push button 31 protrudes from the rear part of the covering 10.

When in the rest position, the button 31 is hidden by safety means 32, which include a slide 33, sliding on the rear part of the covering 10.

A pair of prismatic elements 34 protrude from the slide 33 and are guided slidingly through respective slots 35 made in the rear part of the covering 10.

Plates 36 are made integral with the prismatic elements 34 inside the covering 10.

One end of the rocker arm 30 is introduced into an aperture 37 made in the plates 36.

Each plate 36 forms also, in its upper part, a pair of teeth 38 extending from both sides of the plate.

The teeth 38 couple frictionally with the inner surface of the respective connection 26.

The push button 31 operates a small lever 39, which rotates about a pin 40 located in the region of an opening 41 made in the bottom of the covering 10.

During the ejection of the needle 2, the small lever 39 acts on a pawl 42, which forms a locking means of the first moving element 11, in the loading position.

The pawl 42, while the first moving element 11 is in the loading position, engages the above mentioned opening 41, which houses the small lever 39.

The pawl 42 is hinged to the first moving element 11 by a first pivot 43 located in the region of a lower recess 44 of the first moving element 11.

Likewise, the second moving element 12 is equipped with related locking means, including a second pawl 45 hinged on a second pivot 46 and engaging, when the second moving element is in the loading position, with a corresponding indentation 47 made in the bottom of the covering 10.

The device features also an additional button, which includes a cursor 51, mounted sliding in a seat 50 made in the lower part of the covering 10.

The cursor 51 is integral with a bar 52, which acts on the release small lever 39 of the first pawl 42, passing through a corresponding hole made in the covering 10.

Figure 9:
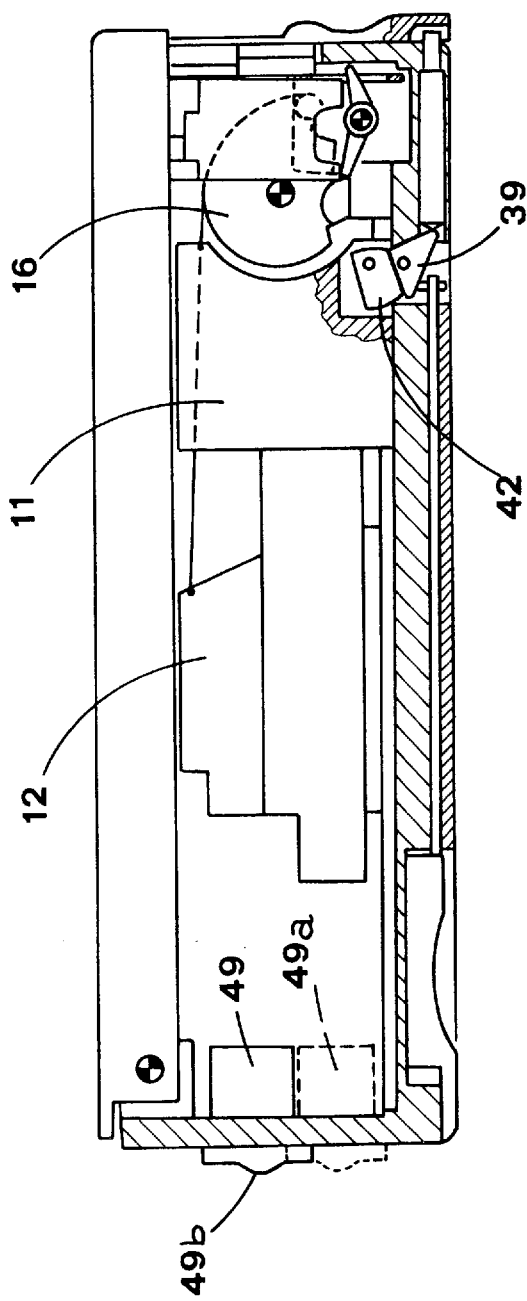

A device 49 for limiting the stroke of the moving elements 11, 12 is situated near the fore inner wall of the covering 10 (see FIGS. 8 and 9).

The limiting device 49 includes a block which slides vertically as shown with broken line 49a in FIG. 9 and which is operated from outside by a corresponding cursor 49b situated near the fore outer wall of the covering 10.

The operation of the described device appears extremely simple.

Immediately before carrying out the biopsy, the operator loads the device by acting on the levers 21, 22, which are situated one beside the other.

Contemporary lowering of the loading levers 21 and 22 provokes a first rotation stroke of the cams 16 and 17 by a first predetermined angle, as shown in FIG. 7, where only the first cam 16 can be seen.

The oscillating prongs of the pliers 24 of the gripping means 23 of the levers 21 and 22 engage the first pair of protrusions 18 of the cams 16 and 17, thus driving the cams 16 and 17 into rotation; the protrusions 18 are hooked by the shoulders 24a of the prongs 24, which are elastically closed by the relative spring 27.

Obviously, the rotation of the cams 16 and 17 determines the sliding of the first and second moving elements 11 and 12 inside the covering 10, against the reaction force of the respective loading springs, not shown, which are preferably extension springs, as has already been said.

When the loading stroke is completed, the end of the rocker arm 30 engages with the first recess 28 of the cams 16 and 17 (see again FIG. 7), preventing the return of the cams 16 and 17 when the loading levers 21 and 22 are released (FIG. 8).

Then, the loading levers 21 and 22 are operated again, so as to provoke a second rotation stroke of the cams 16 and 17 by a second predetermined angle (FIG. 9).

In fact, the oscillating prongs 24 of the gripping pliers 23 of the levers 21 and 22 engage the second pair of protrusions 19 of the cams 16 and 17, driving the cams 16 and 17 to rotate.

When the second loading stroke is completed, the end of the rocker arm 30 engages with the second recess 29 of the cams 16 and 17, thus preventing the return of the cams 16 and 17 when the loading levers 21 and 22 are released.

The rotation of the cams 16 and 17 drive the moving elements 11 and 12 to slide inside the covering 10, against the action of the loading springs, up to the loading position, in which the pawls 42 and 45 engages with the opening 41 and indentation 47 made in the bottom of the covering 10, as seen in detail in FIG. 10.

It is to be noted that during the previously described steps, the slide 33 of the safety means 32 is lowered, so as to prevent an accidental operation of the button 31.

Then, the operator mounts the needle 2 on the already loaded device.

This way is undoubtedly more advantageous, but it is to be noted that the needle can be mounted also when the device is not loaded yet and the needle is in its initial rest position, as seen in FIG. 6, and the moving elements 11 and 12 are brought to touch the fore wall of the covering 10.

The needle 2 is mounted by a suitable mounting device 6 including a support 60, which has a pair of grooves 61, 62.

The respective snap-in members 63, 64 of the cannula 3 and of the stylet 4 of the needle snap into the grooves 61, 62 (FIG. 1).

The support 60 is to be introduced into the lower groove 13 of the covering 10, as shown with the broken line 6a in FIG. 2, so as to couple the snap-in members 63, 64 with corresponding female coupling members 65, 66, which are fastened to the first moving element 11 and the second moving element 12, respectively (see FIGS. 3 and 4).

Therefore, in order to operate the device, it is necessary to move the slide 33 to the raised position, so as to make the button 31 accessible (FIG. 10).

Upward moving of the slide 33 determines also the rotation of the pair of rocker levers 30, acted upon by the plates 36 fastened to the slide 33, so as to release the cams 16 and 17.

The plates 36 couple frictionally with the loading levers 21 and 22 by teeth 38, which couple with the connections 26, as seen in FIG. 13, so as to maintain the loading levers in the lowered position during the subsequent working steps.

When in the lowered position, the gripping means 23 of the levers 21 and 22 do not hinder the reverse rotation of the cams 16 and 17.

Then, the operator introduces the needle 2 through the skin up to the tissue to be sampled.

During this step, the stylet 4 is introduced into the cannula 3, with the pointed portion 4a protruding from the distal end 3a of the cannula 3 (FIG. 5b).

Acting on the button 31, the operator controls the automatic quick sequence forward movement of the stylet 4 and then of the cannula 3, due to the elastic thrust of the springs acting on the moving elements 11 and 12, so as to eject the needle 2.

Figure 11:
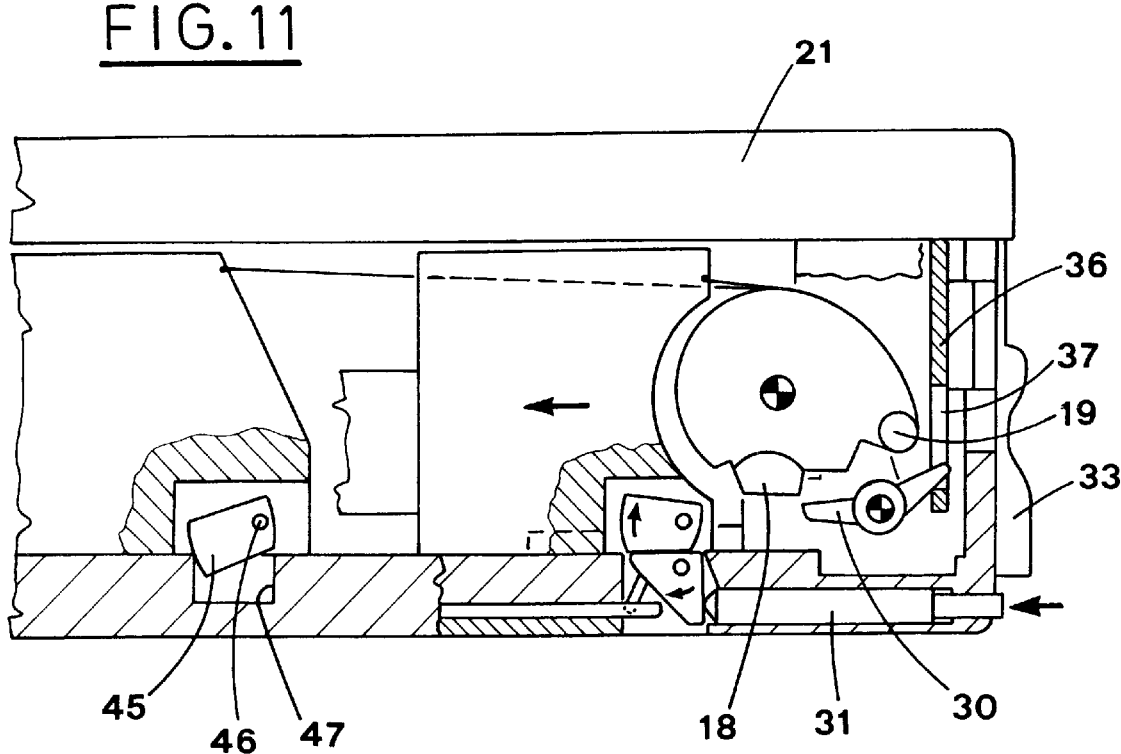

In fact, the push button 31 drives the small lever 39 to rotate, so as to release the pawl 42 from the opening 41, thus freeing the first moving element 11 (FIG. 11).

The forward movement of the first moving element 11 ejects the stylet 4 from the cannula 3, thus uncovering the cavity 5 of the stylet 4 (FIG. 5a).

Figure 12:
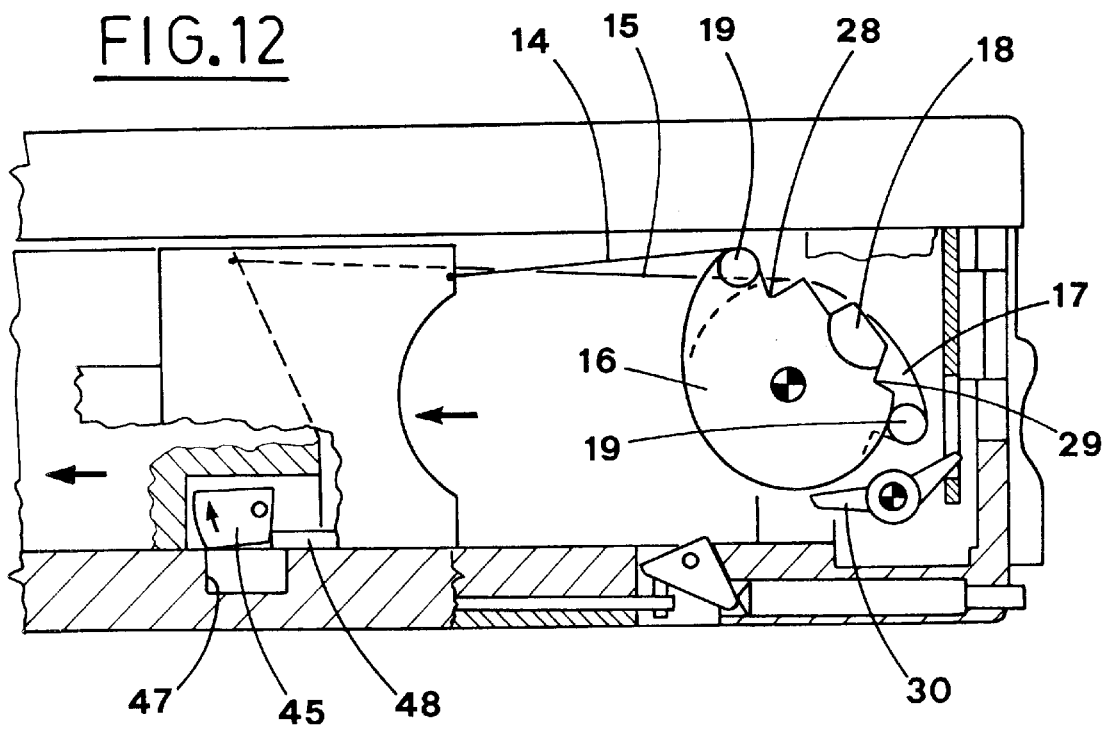

During the forward movement step, the first moving element 11 removes the second pawl 45 from engagement with the indentation 47 by means of a suitable protrusion 48, thus freeing also the second moving element 12 (FIG. 12).

The forward movement of the second moving element 12 makes the cannula 3 slide on the stylet 4, until the cavity 5 of the stylet 4 is wholly covered; the cannula cuts that portion of the tissue which is comprised between the cavity 5 of the stylet and the inner wall of the cannula.

The moving elements 11 and 12 stop against the fore wall of the covering 10.

If required by the use conditions, it is possible to limit the stroke of the moving elements 11 and 12, i.e. the strokes of the cannula 3 and the stylet 4, by moving, through the cursor 49b, the limiting device 49 joined to the fore wall of the covering 10, as shown with broken line 49a in FIG. 9.

The limiting device 49 has a particularly important task in the proposed device, since it allows to adjust the stroke of the needle 2 in relation to the dimensions of the mass, in which the biopsy is being carried out.

It is also possible to eject the needle 2 from the device by acting on the additional cursor 51, which controls, through the bar 52, the rotation of the small lever 39 for releasing the first pawl 42.

After the working steps have been completed, the needle is withdrawn from the patient's body and the bioptic sample, contained inside the cavity 5 of the stylet 4 kept in the cannula 3, is removed.

Therefore, the proposed biopsy needle device fulfills the object of sampling soft tissues in best way.

In particular, the main advantage of the present invention is that it provides an automatic biopsy device, which allows the operator to easily operate the loading system with one hand only.

In fact, in order to load the needle device, the operator needs to press the loading levers 21, 22 with one finger of the hand gripping the covering 10.

Moreover, the double loading step allows to divide the necessary effort, so the operation is not difficult.

The effort is decreased also by the shape of the cams, which allows to reduce the pulling effort on the moving elements.

Another advantage of the present invention derives from the fact that it proposes a biopsy needle device, which considerably facilitates the introduction of the needle into the covering of the device, due to the hooking device 6, which is to be introduced into the groove 13 housing the needle, so as to couple the hooking members 63, 64 with corresponding female members 65, 66, which are fastened to the first moving element 11 and the second moving element 12, respectively.

A further advantage of the present invention is that it proposes a needle device, which is simple to manufacture and safe and precise to use by medical staff.

It will be understood that modifications and variations may be effected without departing from the spirit and scope of the novel concepts of this invention.

What is claimed is:

1. An automatic biopsy device, including:
   a needle formed by a cannula, having a cannula distal end with a cutting rim, and a cannula proximal end;
   a stylet sliding axially inside said cannula and having a stylet distal end with a pointed portion, and a stylet proximal end, said pointed portion protruding from said cannula distal end of said cannula when the stylet is in an advanced position;
   a cavity made in said stylet close to said stylet distal end and aimed at receiving a sample of an organ to be examined;
   a box-like covering;
   a first moving element mounted slidingly inside said box-like covering and aimed at being fastened to said stylet proximal end of said stylet of said needle;
   a second moving element mounted slidingly inside said box-like covering beside said first moving element and aimed at being fastened to said cannula proximal end of said cannula of said needle;
   a first cam and a second cam rotating, independently one from the other, about a transversal axis of said covering, and fastened by flexible means to said moving element and to said second moving element, respectively;
   a first loading lever and a second loading lever arranged side by side and pivoted to said covering, said first loading lever and second loading lever being aimed at driving said first cam and said second cam respectively, into rotation against elastic means, so as to move said first moving element and said second moving element to a loading position;
   first locking means and second locking means for keeping said first moving element and said second moving element, respectively, in said loading position;
   button means for releasing said locking means in said loading position, to operate an ejection of the needle.

2. A device according to claim 1, wherein said loading levers cause, by subsequent operations, a first and a second rotation stroke of said first cam and said second cam, by corresponding predetermined first and second angle, so as to move said first moving element and said second moving element to the loading position.

3. A device according to claim 1, wherein said loading levers are equipped with respective gripping means which engage relative eccentric protrusions of said cams, so as to drive said cams to rotate.

4. A device according to claim 3, wherein said gripping means include pliers formed by a pair of prongs, which are mounted oscillating on said loading levers and which form, on the inner side, respective shoulders, said shoulders engaging elastically said protrusions of said cams due to the thrust of elastic means.

5. A device according to claim 1, wherein said cams form, on related edges, respective recesses for engaging with a rocker arm, as a consequence of a rotation of said loading levers, said rocker arm being rotating about a transversal axis of said covering, so as to maintain said cams in a reached loading position.

6. A device according to claim 1, wherein said first locking means and said second locking means include respective pawls, which are hinged to said moving elements and which engage, when said moving elements are in loading positions, respectively with an opening and an indentation made in a bottom wall of the covering.

7. A device according to claim 6, wherein a small lever, in the region of said opening and operated by button means, acts on said pawl hinged to said first moving element, so as to release said first moving element, with said button sliding in a corresponding seat made in said bottom wall of said covering, so as to control the ejection of the needle.

8. A device according to claim 1, including a safety means with a slide sliding in the rear part of said covering between a lowered position, in which said safety means covers said operating button, and a raised position for preparation of said needle ejection, with said slide carrying, protruding inside the covering, means for releasing said cams joined to said moving elements.

9. A device according to claim 8, wherein said releasing means include a pair of plates, which feature a relative aperture, with one end of a respective rocker arm introduced into said aperture, said rocker arm being rotated about a transversal axis of said covering and aimed at engaging with said cams for maintaining said cams in the reached loading position.

10. A device according to claim 9, wherein said plates have a pair of teeth at their upper part, said teeth extending on both sides of said plates and coupling frictionally with an inner surface of said loading levers.

11. A device according to claim 1, wherein said button means for controlling the release of said locking means include a cursor, mounted slidingly in a seat made in the lower part of said covering and integral with a bar, which engages, through a corresponding hole made in the covering, a small lever for releasing said first locking means.

12. A device according to claim 1, wherein including a mounting device for introduction of said needle, said mounting device including a support featuring a pair of grooves, with respective snap-in members connected to said cannula and stylet provided for engagement with said grooves, with said support aimed at being introduced into a lower groove of said covering, so as to couple said snap-in members with corresponding female members fastened to said first moving element and second moving element, respectively.

13. A device according to claim 1, including also a device limiting the stroke of said moving elements, said limiting device being situated inside the covering and aimed, when brought to its working position, at reducing the oscillation amplitude of said moving elements by a predetermined length.

14. A device according to claim 13, wherein said limiting device includes at least one shaped block, sliding near a fore inner wall of said covering and integral with a respective cursor made in a fore outer wall of the covering.

* * * * *